Nov. 29, 1949. M. GILMORE Plant Pat. 899
DAHLIA PLANT
Filed Dec. 16, 1948
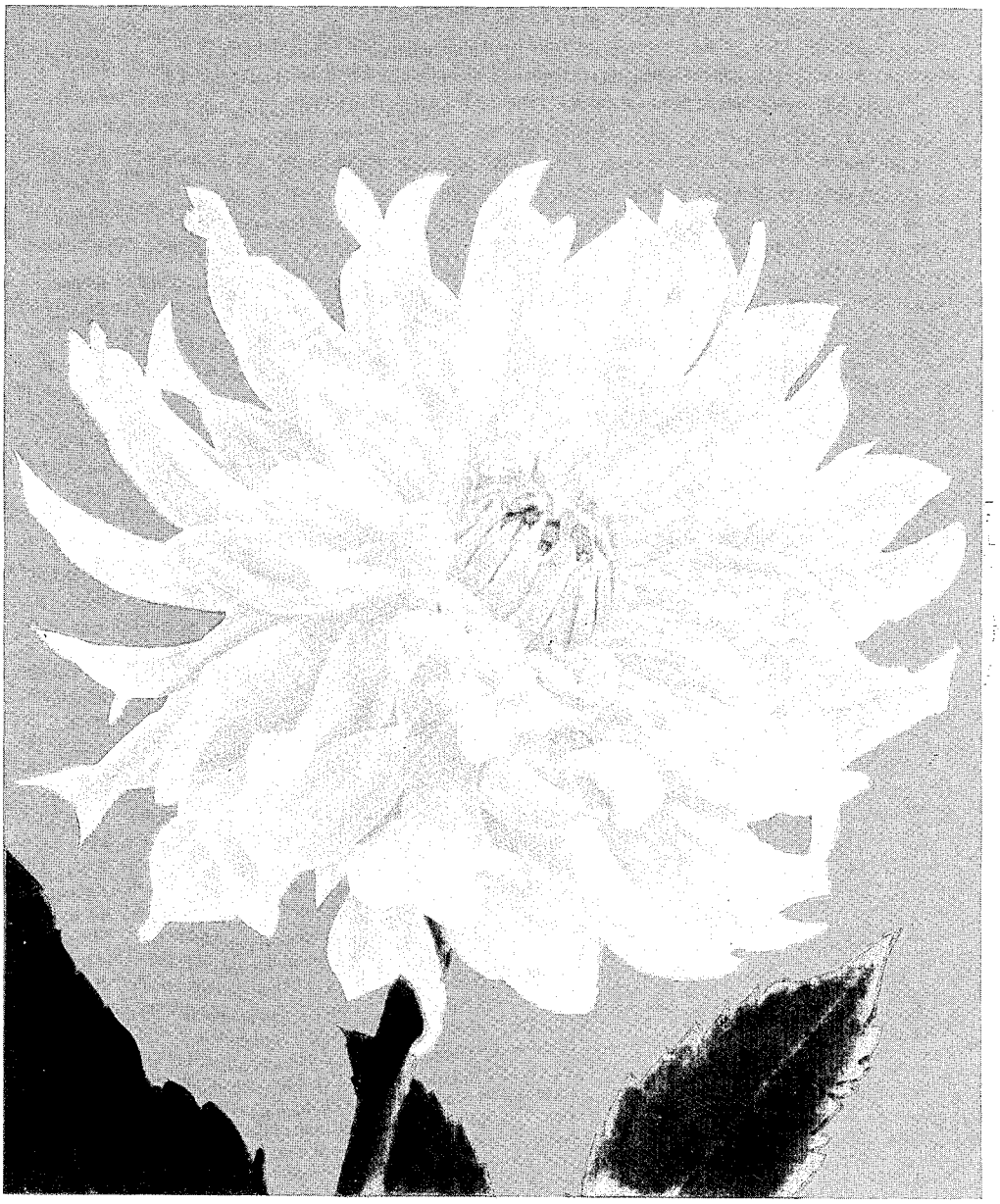
Inventor.
Martin Gilmore
By Robbins & Robb
Attorneys Patented Nov. 29, 1949

Plant Pat. 899

UNITED STATES PATENT OFFICE

899

DAHLIA PLANT

Martin Gilmore, Manchester, Mass.

Application December 16, 1948, Serial No. 65,619

1 Claim. (Cl. 47—60)

The present invention relates to a new and distinct variety of dahlia plant, having as its ultimate objective the combining of certain of the characteristics of each of the parents to produce a variety improved in many respects from the commercial standpoint.

This new variety is the result of crossing the varieties "Jane Cowl" and "Baby Royal," both well known to the trade, especially the former. The improvements achieved reside particularly in the color and keeping quality of the bloom, in its dwarf, sturdy habit of growth and its immunity from insects and disease.

By way of comparison with its parents, "Jane Cowl" is a large, strong spreading plant averaging about six feet in height, having monstrous golden buff blooms suffused with salmon and pink about ten inches in diameter, with only fair keeping quality.

On the other hand, "Baby Royal" is a dwarf, wiry-stemmed plant with an average growth height of about two feet; a profuse bloomer of semi-cactus flowers of bright pink with traces of gold at base of petals and usually less than four inches in diameter, of good keeping quality.

I have been able to combine these parental characteristics into a dwarf variety of distinct color and keeping quality, so much more useful and desirable in the trade than most of the present known varieties of a comparable class.

Asexual reproduction of this new variety shows the foregoing characteristics come true to form and are established.

In the accompanying drawing is illustrated a specimen of the flower and foliage of the new variety.

The following is a detailed description of the new variety, color terminology being in accordance with Ridgway's Color Standards and Nomenclature and ordinary dictionary significance.

The specimens described were grown at Manchester, Massachusetts.

Parentage: Seedling. "Jane Cowl" and "Baby Royal."

Classification: Semi-cactus. *Botanic*—composite.

Blooming habit: Good, blooms early, about July 20th.

Bud:

*Size.*—Medium.

*Form.*—Globular.

Bloom: Size, when fully open, medium; five inches to six inches.

*Disk flower.*—About 45.

*Ray flower.*—About 130, irregular shape, half tubular, slightly curved.

*Borne.*—Singly, on strong, medium length stems.

*Form.*—When first petal opens—globular. When fully opened—somewhat flat.

*Color.*—Center (unopened petals)—Light Yellowish Olive, Plate XXX. Center petals—Rose Doree, Plate I, with Light Cadmium, Plate IV, at base. Cadmium yellow depth color shows plainly in center of open flower, and gradually decreases toward the outer end of petals. Outside petals, Eosine Pink, Plate I, with less light cadmium at base.

Petals: Thin.

*Shape.*—Linear.

*Arrangement.*—Informal.

*Lasting quality.*—On plant—good; as cut flower—very good.

Form of plant: Bush.

Growth: Medium vigorous; upright; compact. Height—24 inches to 30 inches.

Foliage:

*Size.*—Medium.

*Quantity.*—Abundant.

*Color.*—Dark Calla Green and Cerro Green, both Plate V.

*Stem.*—Sturdy. Color—Russett to Mummy Brown, both Plate XV.

*Shape.*—Oval pointed.

*Texture.*—Upper side and under side—smooth.

*Ribs and veins.*—Ordinary.

*Edge.*—Saw toothed.

Wood:

*New wood.*—Color—dark.

*Old wood.*—Color—dark green.

I claim:

A new and distinct variety of dahlia plant, characterized as to novelty by the distinct color of its blooms, their good keeping qualities, by its dwarf, sturdy and unform habits of growth, and its immunity from insect and disease destruction substantially as shown and described.

MARTIN GILMORE.

No references cited.